United States Patent [19]

Carr et al.

[11] 4,443,462
[45] Apr. 17, 1984

[54] ANTIPSYCHOTIC 4-(NAPHTHALENYLOXY)PIPERIDINE DERIVATIVES

[75] Inventors: Albert A. Carr; Robert A. Farr, both of Cincinnati, Ohio

[73] Assignee: Merrell Dow Pharmaceuticals Inc., Cincinnati, Ohio

[21] Appl. No.: 422,819

[22] Filed: Sep. 24, 1982

Related U.S. Application Data

[63] Continuation of Ser. No. 64,305, Aug. 6, 1979, abandoned.

[51] Int. Cl.³ .................. A61K 31/445; C07D 211/44
[52] U.S. Cl. ..................................... 424/267; 546/206
[58] Field of Search ......................... 546/206; 424/267

[56] References Cited

U.S. PATENT DOCUMENTS 3,743,645 7/1973 Helsley .................................. 546/221
3,795,677 3/1974 Carr et al. ......................... 546/225 X
4,145,427 3/1979 Langbein et al. .................... 424/267
4,160,837 7/1979 Paioni ............................. 546/206 X
4,246,268 1/1981 Carr .................................. 424/267

OTHER PUBLICATIONS

Janssen, P., et al., Arz. Forsch., 15, 105 (1965).
Carlsson, A., Am. J. Psychiatry 135(2), 164–173 (1978).

Primary Examiner—Richard A. Schwartz
Attorney, Agent, or Firm—Edlyn S. Simmons

[57] ABSTRACT

Novel compounds of the formula

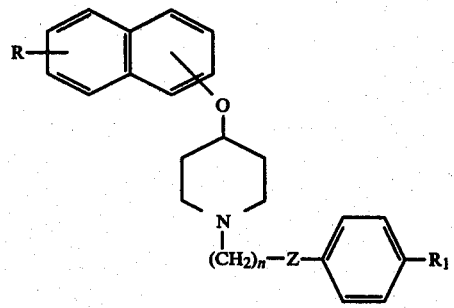

wherein n is an integer of from 2 to 5, R is hydrogen, alkyl, alkoxy, halogen or trifluoromethyl, $R_1$ is hydrogen, alkyl, alkoxy or halogen, and Z is carbonyl or hydroxymethylene and their pharmaceutically acceptable acid addition salts are useful as antipsychotic agents having a low potential for extrapyramidal side effects. The novel compounds are prepared from novel intermediates of formula

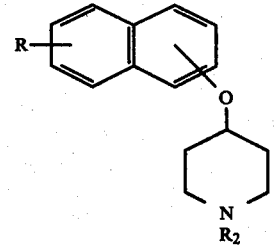

or their salts wherein R has the meanings defined above and $R_2$ is hydrogen, lower alkyl or phenyl(lower alkyl).

13 Claims, No Drawings

ANTIPSYCHOTIC 4-(NAPHTHALENYLOXY)PIPERIDINE DERIVATIVES

This is a continuation, of application Ser. No. 64,305, filed Aug. 6, 1979, now abandoned.

FIELD OF THE INVENTION

This invention relates to novel derivatives of 4-(naphthalenyloxy)piperidines and methods for their preparation. More particularly it relates to new 4-naphthalenyloxypiperidines, useful as chemical intermediates, and their N-(ω-benzoylalkyl) and N-(ω-hydroxy-ω-phenylalkyl)derivatives, useful as neuroleptic tranquilizers whose use does not induce significant extrapyramidal side effects.

DESCRIPTION OF THE PRIOR ART

1-Phenyl-ω-(1-piperidyl)alkanones constitute an important class of central nervous system depressants. Various compounds of this class are claimed, for example, in U.S. Pat. Nos. 3,438,991; 3,518,276; 3,576,810; 3,816,433; 3,888,867 and 3,907,812. Although compounds of this type are often found to have potent antipsychotic activity, their use has been limited by the occurrence of serious extrapyramidal side effects and transient hypotension.

It has now been discovered that the novel ω-(4-naphthalenyloxy-1-piperidyl)-1-phenylalkanones and the corresponding naphthalenyloxy-α-phenyl-1-piperidinalkanols of this invention display potent antipsychotic activity without inducing significant extrapyramidal side effects and with little effect on blood pressure.

SUMMARY OF THE INVENTION

Novel compounds of formula

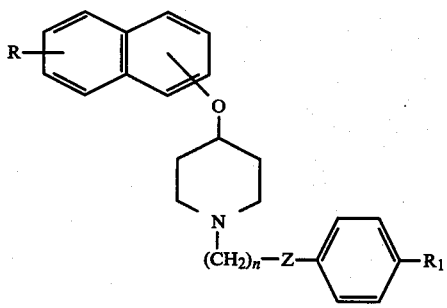

Formula I wherein n is an integer of from 2 to 5; R is hydrogen, alkyl, alkoxy, halogen or trifluormethyl; $R_1$ is hydrogen, alkyl, alkoxy or halogen; and Z is carbonyl or hydroxymethylene, are useful as antipsychotic agents. These antipsychotic compounds may be prepared from intermediates of Formula II

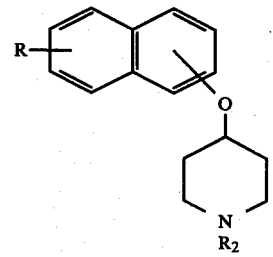

Formula II wherein $R_2$ is hydrogen, lower alkyl or phenyl(lower alkyl) and R has the meaning defined above. Compounds of Formula II are also novel compounds and are included in this invention. Included in the invention are the pharmaceutically acceptable acid addition salts of compounds of Formulas I and II and individual optical isomers of the compounds of Formula I.

DETAILED DESCRIPTION OF THE INVENTION

Compounds of Formula I include ω-[4-(1- and 2-naphthalenyloxy-1-piperidyl)]-1-(4-substituted)phenyl-1-alkanones of Formula III

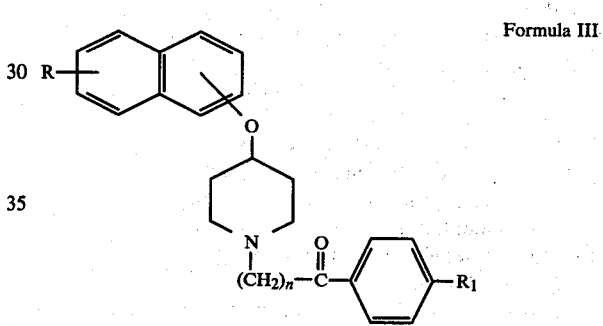

Formula III and 4-(1- and 2-naphthalenyloxy)-α-(4-substituted)phenyl-1-piperidinealkanols of Formula IV

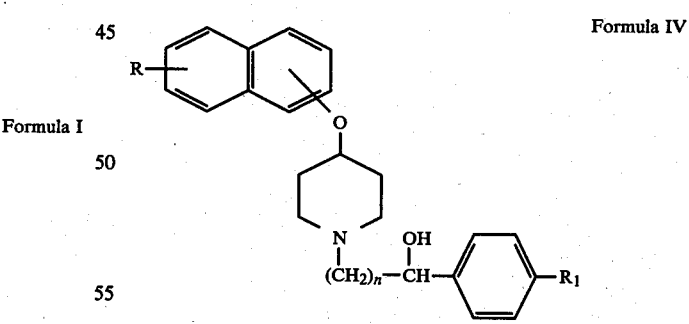

Formula IV wherein n, R and $R_1$ have the meanings defined above, their individual optical isomers, and their pharmaceutically acceptable acid addition salts.

As used herein, alkyl is taken to mean straight or branched chain alkyl groups having from 1 to 4 carbon atoms. Illustrative examples of alkyl groups are methyl, ethyl, propyl and tertiary butyl. Lower alkyl is taken to mean straight chain alkyl of from 1 to 3 carbon atoms. Alkoxy is taken to mean straight or branched chain alkoxy groups having from 1 to 4 carbon atoms. Illustrative examples of alkoxy groups are methoxy, ethoxy and isopropoxy. Halogen is taken to mean fluorine, chlorine or bromine.

The substituent R may be located in any position of the naphthalene ring system other than the position occupied by the (4-piperidyloxy) substituent.

Preferred embodiments of this invention are compounds of Formula I wherein Z is carbonyl; also preferred are embodiments of this invention wherein n is equal to 3. Further preferred embodiments of this invention are compounds of Formula I wherein R is selected from hydrogen and halogen. Preferred embodiments of this invention also include compounds of Formula I wherein $R_1$ is halogen and especially fluorine.

Exemplary compounds of Formula I are:
4-[4-(1-naphthalenyloxy)-1-piperidyl]-1-(4-fluorophenyl)1-butanone,
4-[4-(2-naphthalenyloxy)-1-piperidyl]-1-(4-fluorophenyl)-1-butanone,
4-[4-(6-chloro-2-naphthalenyloxy)-1-piperidyl]-1-(4-fluorophenyl)-1butanone,
3-[4-(5-methoxy-1-naphthalenyloxy)-1-piperidyl]-1-(4-chlorophenyl)-1-propanone,
4-[4-(2-naphthalenyloxy)-1-piperidyl]-1-(4-methylphenyl)-1-butanone,
5-[4-(1-methyl-2-naphthalenyloxy)-1-piperidyl]-1-(4-ethoxyphenyl)-1-pentanone,
4-[4-(8-methoxy-2-naphthalenyloxy)-1-piperidyl]-1-phenyl-1-butanone,
6-[4-(5-fluoro-1-naphthalenyloxy)-1-piperidyl]-1-(4-fluorophenyl)-1-hexanone,
4-[4-(2-trifluoromethyl-1-naphthalenyloxy)-1-piperidinyl]-1-(4-bromophenyl)-1-butanone,
4-(1-naphthalenyloxy)-α-(4-fluorophenyl)-1-piperidinebutanol,
4-(2-naphthalenyloxy)-α-(4-fluorophenyl)-1-piperidinebutanol,
4-(4-trifluoromethyl-2-naphthalenyloxy)-α-phenyl-1-piperidinebutanol,
4-(6-bromo-2-naphthalenyloxy)-α-(4-bromophenyl)-1-piperidinepropanol,
4-(7-isopropyl-1-naphthalenyloxy)-α-(4-fluorophenyl)-1-piperidinepentanol,
4-(3-ethoxy-2-naphthalenyloxy)-α-(4-methoxyphenyl)-1-piperidinebutanol,
4-(2-naphthalenyloxy-α-(4-ethylphenyl)-1-piperidinehexanol,
4-(8-fluoro-1-naphthalenyloxy)-α-(4-fluorophenyl)-1-piperidinebutanol, and
4-(2-methyl-1-naphthalenyloxy)-α-(phenyl)-1-piperidinebutanol.

The invention also includes the pharmaceutically acceptable acid addition salts of compounds of Formula I, which are also active as antipsychotics. Suitable salts include those of inorganic acids, such as hydrochloric, hydrobromic, sulfuric and phosphoric acids; carboxylic acids, such as acetic, propionic, glycolic, lactic, pyruvic, malonic, succinic, fumaric, malic, tartaric, citric, ascorbic, maleic, hydroxymaleic, dihydroxymaleic, benzoic, phenylacetic, 4-aminobenzoic, 4-hydroxybenzoic, anthranilic, cinnamic, salicylic, aminosalicylic, 2-phenoxybenzoic, 2-acetoxybenzoic and mandelic acids; and sulfonic acids, such as methanesulfonic, 2-hydroxyethanesulfonic and p-toluenesulfonic acids.

Novel intermediates for the preparation of compounds of Formula I are compounds of formula II

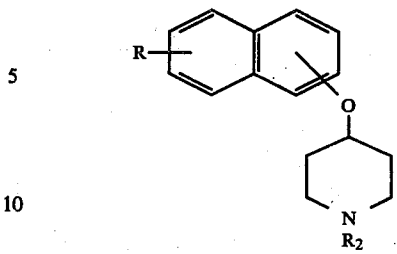

Formula II wherein R has the meaning defined above, and $R_2$ is hydrogen, lower alkyl or phenyl(lower alkyl) and acid addition salts thereof. Preferred embodiments of Formula II are compounds wherein $R_2$ is hydrogen, methyl or phenylmethyl and those wherein R is hydrogen or halogen.

Exemplary compounds of formula II include:
4-(1-naphthalenyloxy)piperidine,
4-(2-naphthalenyloxy)piperidine,
4-(6-chloro-2-naphthalenyloxy)piperidine,
4-(5-methoxy-1-naphthalenyloxy)piperidine,
4-(1-methyl-2-naphthalenyloxy)piperidine,
4-(8-methoxy-2-naphthalenyloxy)piperidine,
4-(5-fluoro-1-naphthalenyloxy)piperidine,
4-(2-trifluoromethyl-1-naphthalenyloxy)piperidine,
4-(6-bromo-2-naphthalenyloxy)piperidine,
4-(7-isopropyl-1-naphthalenyloxy)piperidine,
4-(4-trifluoromethyl-2-naphthalenyloxy)piperidine,
4-(3-ethoxy-2-naphthalenyloxy)piperidine,
4-(8-fluoro-1-naphthalenyloxy)piperidine,
4-(2-methyl-1-naphthalenyloxy)piperidine.
1-methyl-4-(1-naphthalenyloxy)piperidine,
1-methyl-4-(6-chloro-2-naphthalenyloxy)piperidine,
1-methyl-4-(1-methyl-2-naphthalenyloxy)piperidine,
1-methyl-4-(4-trifluoromethyl-2-naphthalenyloxy)-piperidine,
1-ethyl-4-(5-fluoro-1-naphthalenyloxy)piperidine,
1-methyl-4-(7-isopropyl-1-naphthalenyloxy)piperidine,
1-propyl-4-(8-methoxy-2-naphthalenyloxy)piperidine,
1-(phenylmethyl)-4-(2-naphthalenyloxy)piperidine,
1-(2-phenylethyl)-4-(5-methoxy-1-naphthalenyloxy)-piperidine,
1-(phenylmethyl)-4-(2-trifluoromethyl-1-naphthalenyloxy)piperidine,
1-(phenylmethyl)-4-(6-bromo-2-naphthalenyloxy)-piperidine,
1-(phenylmethyl)-4-(3-ethoxy-2-naphthalenyloxy)-piperidine,
1-(3-phenylpropyl)-4-(8-fluoro-1-naphthalenyloxy)-piperidine, and their acid addition salts.

The novel compounds of Formula I are antipsychotic agents useful when administered alone or in the form of pharmaceutical preparations containing the novel compounds in combination with a pharmaceutical carrier as neuroleptic tranquilizers in warm blooded animals. Neuroleptic tranquilizers are useful for treatment of patients showing symptoms of psychoses, such as schizophrenia, or of severe anxiety, agitation or aggressiveness. Such agents have a tranquilizing effect on psychomotor activity, inducing a state of general quiescence in the patient without inducing sleep. Patients suitable for treatment with antipsychotic compositions containing compounds of Formula I include warm blooded animals such as birds, for example turkeys and chickens, and mammals, for example mice, rats, dogs, cats, horses, pigs, cattle, sheep and humans.

Pharmaceutical compositions containing compounds of Formula I may be in solid or liquid form, such as tablets, capsules, powders, solutions, suspensions or emulsions, and may be administered orally, parenterally, for example, intraperitoneally, intramuscularly or subcutaneously, or topically, for example, transdermally or transmucosally. The quantity comprising an effective amount of the novel compound provided in a unit dosage and the nature and quantity of the pharmaceutical carrier will vary widely according to the type of pharmaceutical composition and the body weight of members of the patient population to be treated. The treatment of a patient in need of tranquilizing will provide from 0.002 to 100 mg/kg of body weight of the patient per day to achieve the desired tranquilizing effect. For a human patient this degree of tranquilization may be achieved by means of an antipsychotic composition in the form of tablets containing from 0.2 to 200 mg of the active compound and an appropriate pharmaceutical carrier taken from 1 to 4 times a day. Small unit dosages will be required to achieve a comparable neuroleptic effect in smaller species of animals.

The compounds of general Formula I, together with suitable pharmaceutical carriers, can be in the form of solid unit dosage forms such as tablets, capsules and powders, in the form of a suppository, or embedded in a polymeric matrix. In the preparation of solid unit dosage forms it may be desirable to micronize the compound to be employed. In solid unit dosage forms the compounds can be combined with conventional carriers, for example, binders, such as acacia, corn starch or gelatin; disintegrating agents, such as corn starch, guar gum or alginic acid; lubricants, such as stearic acid or magnesium stearate; and inert fillers, such as lactose, sucrose or corn starch.

The compounds of general Formula I may also be administered as liquid suspensions or solutions using a sterile liquid, such as an oil, water, an alcohol or mixtures thereof, with or without the addition of a pharmaceutically suitable surfactant, suspending agent, or emulsifying agent, for oral, topical or parenteral administration.

For liquid preparations, the compounds of Formula I can be formulated suitably with oils, for example, fixed oils, such as peanut oil, sesame oil and olive oil; fatty acids, such as oleic acid and isostearic acid; and fatty acid esters, such as isopropyl myristate and fatty acid glycerides; with alcohols, such as ethanol, isopropanol and propylene glycol; with water; or with mixtures thereof.

Peanut oil and sesame oil are particularly useful in preparation of formulations for intramuscular injection. Oils can also be employed in the preparation of formulations of the soft gelatin type and suppositories. Water, saline, aqueous dextrose and related sugar solutions and glycerols, such as polyethyleneglycol, may be employed in the preparation of liquid formulations which may suitably contain suspending agents, such as pectin, carbomers, methyl cellulose, hydroxypropyl cellulose or carboxymethyl cellulose, as well as buffers and preservatives.

Illustratively, when 4-[4-(2-naphthalenyloxy)-1-piperidyl]-1-(4-fluorophenyl)-1-butanone hydrochloride was administered intraperitoneally to mice at a dosage of 0.06 mg/kg the aggregate toxicity of d-amphetamine was inhibited in 50% of the mice tested according to the procedures disclosed by J. Burn et al., Arch. Int. *Pharmacodyn.* 113, 290-5-(1955), this demonstrating antipsychotic effectiveness, whereas a dosage level of 0.98 mg/kg of the known tranquilizer chlorpromazine is required to attain a similar level of response. Similarly, compounds of this invention evince neuroleptic activity through the inhibition of pernicious preening in mice tested according to the method disclosed by A. Kandel et al., *Fed. Proc.*, 19 (1, Pt. 1), 24 (1960).

The neuroleptic potency of these compounds is accompained by a reduced tendency to produce extrapyramidal side effects in patients treated with a neuroleptically effective dosage as compared with known antipsychotic agents. Indicative of the reduced extrapyramidal effect of the compounds of this invention, when 4-[4-(2-naphthalenyloxy)-1-piperidyl]-1-(4-fluorophenyl)-1-butanone hydrochloride was administered intraperitoneally to mice, a dosage of 34.0 mg/kg was required to counteract the behavioral effects of apomorphine in 50% of the mice tested according to the general method disclosed by P. A. J. Janssen et al., in *Arzneim-Forsch.* 10, 1003 (1960), whereas only 1.4 mg/kg of chlopromazine was required to attain a similar effect.

Compounds of Formula I are prepared by alkylation of intermediate compounds of Formula IIa,

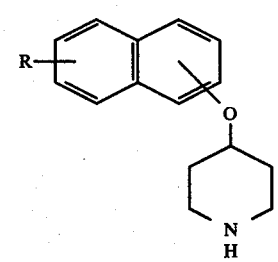

Formula IIa which represent compounds of Formula II wherein $R_2$ is hydrogen and R has the above-identified meaning. Compounds of Formula IIa are themselves prepared by dealkylation or debenzylation of compounds of Formula IIb,

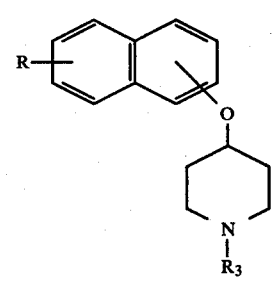

Formula IIb wherein $R_3$ is lower alkyl or phenyl(lower alkyl) and R has the above-defined meaning, which represent compounds of Formula II wherein $R_2$ is lower alkyl or phenyl(lower alkyl). It is thus apparent that all of the compounds of Formula II are useful intermediates for the pharmaceutically useful compounds of Formula I. Compounds of Formula II are also new and represent a part of this invention.

Compounds of Formula IIb are prepared by reaction of an N-substituted-4-piperidinol salt of Formula V

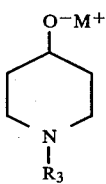

Formula V wherein $R_3$ is lower alkyl or phenyl(lower alkyl) and $M^+$ is an alkali metal cation, such as potassium, sodium or lithium, with a naphthalene fluoride of Formula VI Formula VI wherein R has the meaning defined above, to produce a 1-(lower alkyl) or 1-phenyl(lower alkyl)-4-naphthalenyloxypiperidine of Formula IIb. The compounds of Formula IIa, wherein $R_2$ is hydrogen, are prepared by dealkylation of N-substituted compounds of Formula IIb by means of a chloroformic acid ester of Formula $$R_4O\overset{O}{\underset{\|}{C}}-Cl,$$

wherein $R_4$ is 2,2,2-trichloroethyl, vinyl, substituted vinyl, benzyl, substituted benzyl or cycloalkyl, which is reacted with the compound of Formula IIb in the presence of a proton scavenger, to produce a 1-($R_4$-oxycarbonyl)-4-(naphthanlenyloxy)piperidine of Formula VIII Formula VII wherein R and $R_4$ have the meanings defined above, and removal of the $R_4$-oxycarbonyl group by means of a mild reducing agent, such as zinc dust in acetic acid or methanol, or by acid hydrolysis, as illustrated by the following:

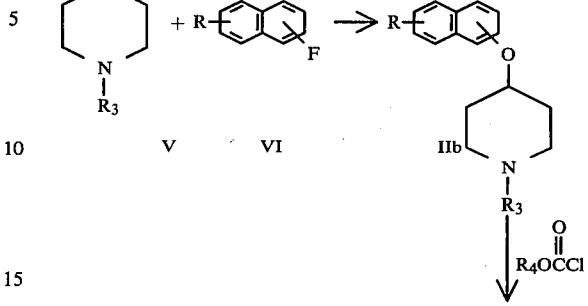

Naphthalene fluorides of Formula VI are well known and may be prepared by methods well known in the art, for example by the methods described by W. Adcock et al., in J. Am. Chem. Soc. 89(2), 386–390 (1967) and in J. Am. Chem. Soc. 98(7), 1701–1711 (1976).

Piperidinol salts of Formula V are prepared by reacting the corresponding 1-lower alkyl- or 1-phenyl(lower-alkyl)-4-piperidinol with a strong base, such as an alkali metal hydride, an alkali metal amide or alkyl lithium according to generally known procedures. The piperidinol salt is reacted with the naphthalene fluoride of Formula VI in the presence of a polar, aprotic solvent at a temperature of from about 50° to about 200° C. or at the boiling temperature of the solvent for from about 1 to about 24 hours. Suitable solvents include tetrahydrofuran, dimethoxyethane, diglyme, dioxane, hexamethylphosphorus triamide, dimethylacetamide, dimethylsulfoxide, 1-methyl-2-pyrrolidone, sulfolane and, especially, dimethyl formamide.

The reaction is quenched and the resulting N-substituted compound of Formula IIb or its acid addition salt is isolated by conventional means, for example, the reaction mixture may be filtered and the solvent removed, isolating the product, which is purified by recrystallization and dried. Suitable solvents for recrystallization are, for example, lower aliphatic alcohols, such as methanol, ethanol and isopropanol; ketones, such as acetone and butanone; esters, such as ethyl acetate; hydrocarbons, such as hexane; and combinations thereof.

The thus prepared 1-lower alkyl- or 1-phenyl(lower-alkyl)-4-(naphthalenyloxy)piperidine of Formula IIb is then reacted with an ester of chloroformic acid in the presence of an aprotic solvent and, preferably, an acid scavenger to form a carbamate of formula VII, which is subsequently cleaved to yield the corresponding 1-unsubstituted-4-(naphthalenyloxy)piperidine of Formula IIa. Suitable chloroformic acid esters are those which yield $R_4$-oxycarbonyl substituents which may be cleaved from the nitrogen atom of the compound of Formula VII hydrolytically or by reducing conditions under which the naphthalene ring is not hydrogenated.

Such chloroformic acid esters include the 2,2,2-trichloroethyl ester, which may be cleaved by reduction with zinc dust or by electrolysis; the benzyl ester, benzyl esters substituted by phenyl, methoxy, methyl, phenylazo, cyano, bromo or chloro, vinyl esters, and cycloalkyl esters, such as the cyclohexyl, cyclopentyl, adamantyl and isobornyl esters, which may be cleaved by acid hydrolysis by means of strong acids, such as hydrochloric or hydrobromic acids, or by means of mild acids, such as trifluoroacetic acid, in suitable solvents. Chloroformic acid esters suitable for displacing alkyl and benzyl substituents from tertiary amines and methods suitable for the cleavage of the various $R_4$-oxycarbonyl groups from the nitrogen atoms are described by M. Bodanszky et al., in *Peptide Synthesis*, 2nd Edition (John Wiley & Sons) p. 21–37 (1976) and by R. Olofson et al. in U.S. Pat. No. 3,905,981, which are hereby incorporated by reference. The preferred chloroformic acid ester for the dealkylation of compounds of Formula II wherein $R_2$ is lower alkyl or phenyl(-lower alkyl) is 2,2,2-trichloroethyl chloroformate.

Suitable solvents for the reaction of an N-substituted compound of Formula IIb with a chloroformic acid ester are aprotic organic solvents, for example, ethers, such as diethyl ether and tetrahydrofuran, aromatic hydrocarbons, such as toluene and benzene, chlorinated hydrocarbons, such as chloroform, dichloroethane and methylene chloride, or mixtures thereof. The preferred solvent is methylene chloride. The reaction may be carried out in the presence of a small amount, for example, 1%–5% by weight of the amount of the compound of Formula IIb, of a proton scavenger, which may be an inorganic base, such as sodium or potassium carbonate, a strong organic base, such as triethylamine, or a mixture thereof. The reaction mixture is maintained at a temperature between about 0° C. and the reflux temperature of the solvent for from about 1 to about 96 hours. The thus obtained 1-($R_4$-oxycarbonyl)-4-(naphthalenyloxy)piperidine of Formula VII is isolated, for example, by extraction into an organic solvent and evaporation of the solvent, according to generally known procedures, and the $R_4$-oxycarbonyl group cleaved by an appropriate method.

In the preferred embodiment of this invention, an N-lower alkyl- or N-phenyl(lower alkyl)-substituted compound of Formula IIb is refluxed in methylene chloride with a slight excess, for example, from 1.01 to 1.3 equivalents, preferably about 1.1 equivalents, of 2,2,2-trichloroethyl chloroformate in the presence of a trace amount of a proton scavenger for from about 6 to about 24 hours at a temperature of from about 15° to about 40° C., preferably at room temperature. The product is extracted into ether, washed with dilute acid and concentrated in vacuo. The resulting 1-(2,2,2-trichloroethoxycarbonyl)-4-(naphthalenyloxy)piperidine is dissolved in a solvent selected from acetic acid, aqueous acetic acid, a lower alkanol, such as methanol, an aqueous lower alkanol, and, preferably, a mixture of acetic acid, water and an ether, such as tetrahydrofuran. At a temperature of from about 0° to 50° C., preferably at room temperature, from 1 to 5 equivalents, preferably about 2 equivalents, of zinc dust is added gradually with stirring, and the reaction allowed to proceed for from about 1 to about 6 hours until gas evolution ceases. The solvents are evaporated and the N-unsubstituted compound of Formula IIa separated from the residual zinc salts by basification, extraction into an organic solvent, washing to remove water soluble impurities, conversion to a water-soluble acid addition salt, washing with organic solvents to remove neutral organic impurities and rebasification. The N-unsubstituted compound is recrystallized by conventional methods, preferably in the form of its acid addition salt, from suitable solvents, such as lower aliphatic alcohols, ketones, esters and combinations thereof.

Free bases of Formula II prepared by the above-mentioned method may be converted to the acid addition salts by reaction with a suitable acid according to generally known procedures.

The compounds of Formula I are prepared by reacting a piperidine derivative of Formula IIa, wherein $R_2$ is hydrogen, with a small excess of an $\omega$-haloalkyl phenyl ketone or an $\omega$-halo-1-phenyl-1-alkanol of structure VIII in the presence of an excess of an acid acceptor, such as, for example, sodium bicarbonate, potassium bicarbonate, sodium carbonate or potassium carbonate, and optionally a small amount of potassium iodide, in a suitable solvent. If desired, 2 or more equivalents of the piperidine derivative of Formula II relative to compound VIII may be used instead of the mineral base acid acceptor. The compounds of Formula I may also be prepared from the acid addition salt of the compound of Formula IIa by reacting the acid addition salt with a compound of structure VIII in the presence of at least 2 equivalents of the mineral base acid acceptor. The reaction mixture may be reacted over a wide range of temperatures. Generally, a reaction temperature of from about 20° to 180° C. is employed. The reaction is conducted over a period of from 1 to 4 days, during which time any evolved water may be collected. As examples of suitable solvents for this reaction, there may be mentioned toluene, xylene, chlorobenzene, methyl isobutyl ketone and lower aliphatic alcohols, such as ethanol, propanol and butanol.

After completion of the reaction, the product is isolated by conventional means, for example, the reaction mixture may be filtered and the solvent removed, isolating the product. Alternately, the filtrate may be treated with an ethereal solution of a suitable mineral or organic acid to give the corresponding salt of the product. The crude product is filtered off, purified by recrystallization and dried. Suitable solvents for recrystallization are, for example, lower aliphatic alcohols, such as methanol, ethanol and isopropanol; ketones, such as acetone and butanone; nitriles, such as acetonitrile; and combinations thereof.

The general method for the preparation of the compounds of Formula I can be represented by the following reaction scheme

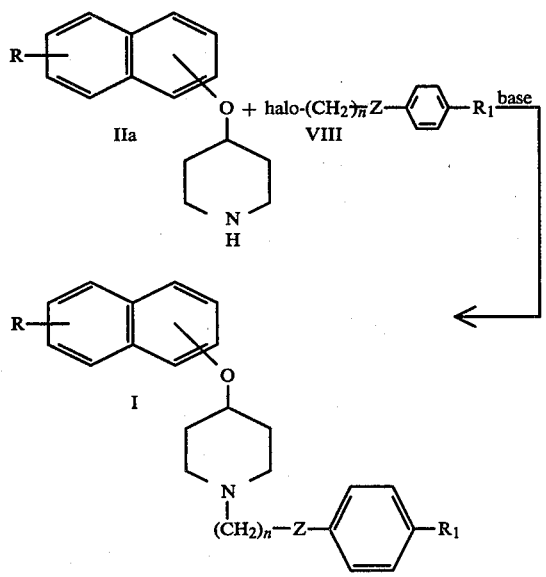

wherein n, R, $R_1$ and Z are as hereinabove defined and halo is a reactive halogen, such as bromine, chlorine or iodine.

Compounds of Formula VIII are commercially available or may be prepared by methods well known in the art. Compounds of Formula VIII wherein Z is C=O may, for example, be prepared by reacting the appropriate ω-haloalkanoyl halide and a (substituted)benzene in the presence of a Lewis acid, such as aluminum chloride, or by reacting a (4-substituted)phenyl Grignard reagent with an appropriate ω-haloalkylnitrile. Compounds of Formula VIII wherein Z is CHOH may be prepared by reduction by means of chemical reducing agents or catalytic hydrogenation of the corresponding 1-(4-substituted)phenyl-ω-haloalkanones of Formula VIII prepared as described above or by reaction of a (4-substituted)phenyl Grignard reagent with an appropriate ω-haloalkanaldehyde.

3-(4-Naphthalenyloxy-1-piperidyl)-1-phenylpropanones, compounds of Formula III wherein n is equal to 2, may also be prepared by reacting compounds of Formula II wherein $R_2$ is hydrogen with an appropriate acetophenone and formaldehyde.

4-(Naphthylenyloxy)-1-piperidinealkanols of Formula IV may be prepared by reduction of alkanones of Formula III. Suitable methods for reducing ketones to alcohols are well known in the art, and include catalytic hydrogenation and reduction by chemical reducing agents.

For catalytic reduction, a ketone of Formula III may, for example, be dissolved in a solvent, such as acetic acid, ethyl acetate, or a lower aliphatic alcohol, such as methanol or isopropanol, and the solution agitated in the presence of hydrogen at from about 1 to about 4 atmospheres of pressure and room temperature, that is about 20°–25° C., in the presence of a suitable catalyst, such as platinum, platinum oxide or rhodium, until one equivalent of hydrogen is consumed.

Alternatively, the ketone of Formula III may be reduced by reaction with a suitable chemical reducing agent. For example, the ketone may be refluxed in ether for from 1 to 5 hours with a metal hydride, for example, lithium aluminum hydride or diborane, or reacted for from about ½ to 8 hours at a temperature of from 0° C. to the reflux temperature of a lower aliphatic alcohol solvent, such as methanol or ethanol, with a metal borohydride, such as sodium borohydride or potassium borohydride, to yield an alcohol of Formula IV. Additional reagents suitable for the reduction of a ketone to an alcohol will be obvious to one skilled in the art.

Compounds of Formula I prepared in the form of free bases may be converted to their acid addition salts by reaction with a pharmaceutically acceptable acid.

The optical isomers of optically active compounds of Formula I may be separated by means of any suitable resolving agent. For example, the optical isomers of compounds of Formula I wherein Z is hydroxymethylene may be separated by using a (+)- or (−)-binaphthylphosphoric acid derivative or a salt of said derivative and an optically active base by the method described by R. Viterbo et al., in *Tetrahedron Letters* 1971 (48), pp. 4617-20.

EXAMPLE 1

4-(2-Naphthalenyloxy)-1-(phenylmethyl)piperidine hydrochloride

To a stirred suspension of 1.80 g (37.5 mmole) of pentane washed 50% sodium hydride dispersion in 50 ml of dry dimethylformamide under argon is added a solution of 4.75 g (25.0 mmole) of 1-phenylmethyl-4-piperidinol in 20 ml of dry dimethylformamide followed by a solution of 3.83 g (26.2 mmole, 1.05 eq.) of 2-fluoronaphthalene in 20 ml of dimethylformamide. The mixture is heated at 75° C. for 23 hours, cooled, poured into ice water and extracted twice with ether. The extracts are washed with water and brine, dried over magnesium sulfate and filtered. The filtrate is treated with HCl/methanol and the resulting 4-(2-naphthalenyloxy)-1-(phenylmethyl)piperidine hydrochloride, recrystallized from butanone/methanol. M.P. 242°–244° C.

EXAMPLE 2

4-(1-Naphthalenyloxy)-1-phenylmethylpiperidine hydrochloride

When in the procedure of Example 1, 1-fluoronaphthalene is substituted for 2-fluoronaphthalene, 4-(1-naphthalenyloxy)-1-(phenylmethyl)piperidine hydrochloride is produced. M.P. 222°–224° C.

EXAMPLE 3

4-(5-Methoxy-1-naphthalenyloxy)-1-(phenylmethyl)-piperidine hydrochloride

When in the procedure of Example 1, 5-methoxy-1-fluoronaphthalene is substituted for 2-fluoronaphthalene, 4-(5-methoxy-1-naphthalenyloxy)-1-(phenylmethyl)piperidine hydrochloride is produced.

EXAMPLE 4

4-(1-Methyl-2-naphthalenyloxy)-1-methylpiperidine hydrochloride

When in the procedure of Example 1, 1-methyl-2-fluoronaphthalene is substituted for 2-fluoronaphthalene and 1-methyl-4-piperidinol is substituted for 1-phenylmethyl-4-piperidinol, 4-(1-methyl-2-naphthalenyloxy)-1-methylpiperidine hydrochloride is produced.

EXAMPLE 5

4-(4-Trifluoromethyl-2-naphthalenyloxy)-1-methyl-piperidinol hydrochloride

When in the procedure of Example 1, 4-trifluoromethyl-2-fluoronaphthalene is substituted for 2-fluoronaphthalene and 1-methyl-4-piperidinol is substituted for 1-phenylmethyl-4-piperidinol, 4-(4-trifluoromethyl-2-naphthalenyloxy)-1-methylpiperidine hydrochloride is produced.

EXAMPLE 6

4-(5-Fluoro-1-naphthalenyloxy)-1-ethylpiperidine hydrochloride

When in the procedure of Example 1, 1,5-difluoronaphthalene is substituted for 2-fluoronaphthalene and 1-ethyl-4-piperidinol is substituted for 1-phenylmethyl-4-piperidinol, 4-(5-fluoro-1-naphthalenyloxy)-1-ethylpiperidine hydrochloride is produced.

EXAMPLE 7

4-(2-Naphthalenyloxy)piperidine hydrochloride

To a stirred solution of 64.6 g (0.204 mole) of 4-(2-naphthalenyloxy)-1-phenylmethylpiperidine in 500 ml of methylene chloride is added 37.0 ml (0.268 mole) of 2,2,2-trichloroethyl chloroformate and about 200 mg. of potassium carbonate. The mixture is stirred at room temperature for 48 hours and poured into a volume of ether and water. The organic phase is washed with dilute hydrochloric acid and aqueous potassium carbonate, dried over magnesium sulfate, and concentrated in vacuo.

The resulting 1-(2,2,2-trichloroethoxycarbonyl)-4-(2-naphthalenyloxy)piperidine is dissolved in a mixture of 250 ml of acetic acid, 250 ml of tetrahydrofuran and 125 ml of water. 28.5 g (0.436 mole) of zinc dust is added in portions with stirring and the exothermic reaction allowed to proceed for 2½ hours. The mixture is filtered and the solvents are removed in vacuo. The residue is partitioned between ether and aqueous sodium hydroxide and the organic phase washed with water and extracted with dilute aqueous hydrochloric acid. The acid extracts are washed with ether, made basic with sodium hydroxide and extracted into ether and toluene and the organic solution washed, dried over magnesium sulfate and concentrated in vacuo to yield 4-(2-naphthalenyloxy)piperidine, which is redissolved in ethanol/ether and treated with dry HCl, and the hydrochloride salt recrystallized from butanone/methanol. M.P. 229.5°–231.5° C.

EXAMPLE 8

4-(1-Naphthalenyloxy)piperidine hydrochloride

When in the procedure of Example 7, 4-(1-naphthalenyloxy)-1-phenylmethyl)piperidine is substituted for 4-(2-naphthalenyloxy)-1-phenylmethyl)piperidine, 4-(1-naphthalenyloxy)piperidine hydrochloride is produced.

EXAMPLE 9

4-(4-Trifluoromethyl-2-naphthalenyloxy)piperidine hydrochloride

When in the procedure of Example 7, 4-(4-trifluoromethyl-2-naphthalenyloxy)-1-methylpiperidine is substituted for 4-(2-naphthalenyloxy)-1-(phenylmethyl)-piperidine, 4-(4-trifluoromethyl-2-naphthalenyloxy)-piperidine hydrochloride is produced.

EXAMPLE 10

4-(5-Fluoro-1-naphthalenyloxy)piperidine hydrochloride

When in the procedure of Example 7, 4-(5-fluoro-1-naphthalenyloxy)-1-ethylpiperidine is substituted for 4-(2-naphthalenyloxy)-1-(phenylmethyl)piperidine, 4-(5-fluoro-1-naphthalenyloxy)piperidine is produced.

EXAMPLE 11

4-(5-Methoxy-1-naphthalenyloxy)piperidine hydrochloride

A solution of 18.4 g (50 mmole) of 4-(5-methoxy-1-naphthalenyloxy)-1-(phenylmethyl)piperidine in 10 ml of 1,2-dichloroethane is added gradually to a chilled solution of 65 mmole of vinyl chloroformate in 50 ml of 1,2-dichloroethane and the mixture stirred at room temperature for 4 hours and concentrated in vacuo.

The thus obtained 4-(5-methoxy-1-naphthalenyloxy)-1-(vinyloxycarbonyl)piperidine is stirred for 2 hours with 2 N HCl in methanol to yield 4-(5-methoxy-1-naphthalenyloxy)piperidine hydrochloride.

EXAMPLE 12

4-(1-Methyl-2-naphthalenyloxy)piperidine hydrochloride

When in the procedure of Example 11 4-(1-methyl-2-naphthalenyloxy)-1-methylpiperidine is reacted with benzyl chloroformate, the resulting 4-(1-methyl-2-naphthalenyloxy)-1-(phenylmethoxycarbonyl)piperidine yields upon hydrolysis 4-(1-methyl-2-naphthalenyloxy)-piperidine hydrochloride.

EXAMPLE 13

4-[4-(2-Naphthalenyloxy)-1-piperidyl]-1-phenyl-1-butanone hydrochloride a solution of 5.67 g (25 mmoles) of 4-(2-naphthalenyloxy)piperidine, 5.0 g (27.4 mmole) of 4-chloro-1-phenyl-1-butanone, 0.1 g of potassium iodide and 4.5 g potassium bicarbonate in 100 ml of toluene is heated for 48 hours with stirring on a steam bath. The mixture is partitioned between 100 ml portions of methylene chloride/ether and water and the organic phase dried over $MgSO_4$. A solution of an excess of HCl in ether is added and the resulting precipitate recrystallized from methanol/butanone to yield 4-(2-naphthalenyloxy-1-piperidyl)-1-phenyl-1-butanone hydrochloride.

EXAMPLE 14

4-[4-(2-Naphthalenyloxy)-1-piperidyl]-1-(4-fluorophenyl)-1-butanone hydrochloride When in the procedure of Example 13, 4-chloro-1-(4-fluorophenyl)-1-butanone is substituted for 4-chloro-1-phenyl-1-butanone; 4-[4-(2-naphthalenyloxy)-1-piperidyl]-1-(4-fluorophenyl)-1-butanone hydrochloride is produced. M.P. 219°–221.5° C.

EXAMPLE 15

4-[4-(1-Naphthalenyloxy)-1-piperidyl]-1-(4-fluorophenyl)-1-butanone hydrochloride When in the procedure of Example 13, 4-chloro-1-(4-fluorophenyl)-1-butanone is substituted for 4-chloro-1-phenyl-1-butanone and 4-(1-naphthalenyloxy)piperidine hydrochloride is substituted for 4-(2-naphthalenyloxy)-piperidine hydrochloride, 4-[4-(1-naphthalenyloxy)-1-piperidyl]-1-(4-fluorophenyl)-1-butanone hydrochloride is produced. M.P. 220°–222.5° C.

EXAMPLE 16

3-[4-(5-Methoxy-1-naphthalenyloxy)-1-piperidyl]-1-(4-chlorophenyl)-1-propanone hydrochloride When in the procedure of Example 13, 4-(5-methoxy-1-naphthalenyloxy)piperidine hydrochloride is substituted for 4-(2-naphthalenyloxy)piperidine hydrochloride and 3-chloro-1-(4-chlorophenyl)-1-propanone substituted for 4-chloro-1-phenyl-1-butanone, 3-[4-(5-methoxy-1-naphthalenyloxy)-1-piperidyl]-1-(4-chlorophenyl)-1-propanone hydrochloride is produced.

EXAMPLE 17

5-[4-(2-Naphthalenyloxy)-1-piperidyl]-1-(4-methylphenyl)-1-pentanone hydrochloride When in the procedure of Example 13, 5-chloro-1-(4-methylphenyl)-1-pentanone is substituted for 4-chloro-1-phenyl-1-butanone, 5-[4-(2-naphthalenyloxy-1-piperidyl]-1-(4-methylphenyl)-1-pentanone hydrochloride is produced.

EXAMPLE 18

4-[4-(1-Methyl-2-naphthalenyloxy)-1-piperidiyl]-1-(4-fluorophenyl)-1-butanone

A solution of 3.47 g of (12.5 mmole) of 4-(1-methyl-2-naphthalenyloxy)piperidine, 2.63 g (13.1 mmole) of 4-chloro-1-(4-fluorophenyl)-1-butanone, 5.2 g (52 mmole) of potassium bicarbonate and a pinch of potassium iodide in 60 ml of toluene is heated at reflux for 80 hours. The mixture is partitioned between toluene and water and the organic phase washed with brine, dried over magnesium sulfate, and concentrated in vacuo to yield 4-[4-(1-methyl-2-naphthalenyloxy)-1-piperidyl]-1-(4-fluorophenyl)-1-butanone.

EXAMPLE 19

6-[4-(4-Trifluoromethyl-2-naphthalenyloxy)-1-piperidyl]-1-(4-methoxyphenyl)-1-hexanone When in the procedure of Example 18, 4-(4-trifluoromethyl-2-naphthalenyloxy)piperidine is substituted for 4-(1-methyl-2-naphthalenyloxy)piperidine and 6-bromo-1-(4-methoxyphenyl)-1-hexanone substituted for 4-chloro-1-(4-fluorophenyl)-1-butanone, 6-[4-(4-trifluoromethyl-2-naphthalenyloxy)-1-piperidyl]-1-(4-methoxyphenyl)-1-hexanone is obtained.

EXAMPLE 20

α-(4-Fluorophenyl)-4-(1-methyl-2-naphthalenyloxy)-1-piperidinebutanol

When in the procedure of Example 18, 4-chloro-1-(4-fluorophenyl)butanol substituted for 4-chloro-1-(4-fluorophenyl)-1-butanone, α-(4-fluorophenyl)-4-(1-methyl-2-naphthalenyloxy)-1-piperidinebutanol is produced.

EXAMPLE 21

α-Phenyl-4-(5-fluoro-1-naphthalenyloxy)-1-piperidinepropanol

When in the procedure of Example 18, 4-(5-fluoro-1-naphthalenyloxy)piperidine is substituted for (1-methyl-2-naphthalenyloxy)piperidine and 3-bromo-1-phenyl-propanol substituted for 4-chloro-1-(4-fluorophenyl)-1-butanone, α-phenyl-4-(5-fluoro-1-naphthalenyloxy)-1-piperidinepropanol is obtained.

EXAMPLE 22

3-[4-(5-Methoxy-1-naphthalenyloxy)-1-piperidyl]-1-(4-fluorophenyl)-1-propanone

A mixture of 25.5 g (0.1 mole) of 4-(5-methoxy-1-naphthalenyloxy)piperidine, 9 g (0.3 mole) of paraformaldehyde and 13.8 g (0.1 mole) of 4'-fluoroacetophenone in 100 ml of isopropyl alcohol containing 2 drops of concentrated hydrochloric acid is refluxed for 24 hours. The mixture is filtered and the filtrate concentrated to about 100 ml and cooled. The resulting precipitate is recrystallized from ethanol to give 3-[4-(5-methyl-1-naphthalenyloxy)piperidyl]-1-(4-fluorophenyl)-1-propanone.

EXAMPLE 23

α-(4-Fluoropenyl)-4-(2-naphthalenyloxy)-1-piperidinebutanol

To 8.0 g (0.02 mole) of 4-[4-(2-naphthalenyloxy)-1-piperidyl]-1-(4-fluorophenyl)-1-butanone HCl in 50 ml of methanol is added 1.1 g (0.02 mole) of sodium methoxide and then 2.7 g (0.05 mole) of potassium borohydride and the mixture stirred at room temperature for 2 hours. The methanol is removed at reduced pressure on a steam bath after which 50 ml of 10% sodium hydroxide solution is added. The mixture is stirred for 15 minutes and 100 ml of chloroform is added. Stirring is continued for ½ hour. The chloroform layer is separated and combined with two 25 ml chloroform extracts of the aqueous phase, washed with water and with brine, dried over $MgSO_4$, filtered and concentrated to a solid. The solid material is recrystallized from ethanol/water to give α-(4-fluorophenyl)-4-(2-naphthalenyloxy)-1-piperidinebutanol.

EXAMPLE 24

α-(4-Methoxyphenyl)-4-(4-trifluoromethyl-2-naphthalenyloxy)-1-piperidinehexanol

When in the procedure of Example 23, 6-[4-(4-trifluoromethyl-2-naphthalenyloxy)-1-piperidyl]-1-(4-methoxyphenyl)-1-hexanone hydrochloride is substituted for 4-[4-(2-naphthalenyloxy)-1-piperidyl]-1-(4-fluorophenyl)-1-butanone, α-(4-methoxyphenyl)-4-(4-trifluoromethyl-1-naphthalenyloxy)-1-piperidinehexanol is obtained.

EXAMPLE 25

Tablet Formulation

An illustration of a representative tablet formulation of an active compound of this invention is as follows:

|   |   | Per Tablet |
|---|---|---|
| (a) | 4-[(2-naphthalenyloxy)-1-piperidyl]-1-(4-fluorophenyl)-1-butanone hydrochloride | 25.0 mg |
| (b) | Wheat starch | 3.5 mg |
| (c) | Lactose | 10.0 mg |
| (d) | Magnesium stearate | 0.5 mg |

A granulation obtained upon mixing lactose with the starch and granulated starch paste is dried, screened and mixed with the active ingredient and magnesium stearate. The mixture is compressed into tablets weighing 39.0 mg each.

EXAMPLE 26

Gelatin Capsule Formulation

An illustrative composition for hard gelatin capsules is as follows:

|  |  | Mg |
|---|---|---|
| (a) | 4-[4-(2-naphthalenyloxy)-1-piperidyl]-1-(4-fluorophenyl)-1-butanone hydrochloride | 10 |
| (b) | Talc | 5 |
| (c) | Lactose | 100 |

The formulation is prepared by passing the dry powders of (a) and (b) through a fine mesh screen and mixing them well. The powder is then filled into hard gelatin capsules at a net fill of 115 mg per capsules.

EXAMPLE 27

Injectable Suspension Formulation

An illustrative composition for an injectable suspension is the following 1 ml ampul for an intramuscular injection.

|  |  | Weight Percent |
|---|---|---|
| (a) | 4-[4-(2-naphthalenyloxy)-1-piperidyl]-1-(4-fluorophenyl)-1-butanone (particle size <10μ) | 1.0 |
| (b) | Polyvinylpyrrolidone (M.W. 25000) | 0.5 |
| (c) | Lecithin | 0.25 |
| (d) | Water for injection to make | 100.0 |

The materials (a)–(d) are mixed, homogenized, and filled into 1 ml ampules which are sealed and autoclaved 20 minutes at 121° C. Each ampul contains 10 mg per ml of novel compound (a).

We claim:

1. A compound of the formula

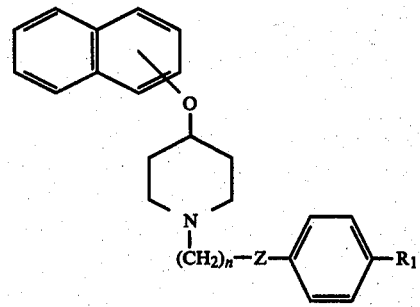

wherein n is an integer of from 2 to 5; $R_1$ is selected from hydrogen, halogen, straight or branched alkyl of from 1 to 4 carbon atoms, and straight or branched alkoxy of from 1 to 4 carbon atoms; and Z is selected from carbonyl and hydroxymethylene; an individual optical isomer, or a pharmaceutically acceptable acid addition salt thereof.

2. A compound of claim 1 wherein Z is carbonyl.

3. A compound of claim 1 wherein n is 3.

4. A compound of claim 1 wherein $R_1$ is halogen.

5. A compound of claim 4 wherein $R_1$ is fluorine.

6. A compound of claim 1 which is 4-[4-(2-naphthalenyloxy)-1-piperidyl]-1-(4-fluorophenyl)-1-butanone or a pharmaceutically acceptable acid addition salt thereof.

7. A compound of claim 1 which is 4-[4-(1-naphthalenyloxy)-1-piperidyl]-1-(4-fluorophenyl)-1-butanone or a pharmaceutically acceptable acid addition salt thereof.

8. An antipsychotic composition comprising an antipsychotically effective amount of a compound of claim 1 and a pharmaceutical carrier.

9. A composition of claim 8 comprising from 0.2 to 200 mg of the compound in unit dosage form.

10. A method of obtaining tranquilizing effects in a patient in need thereof comprising administering to said patient a tranquilizing amount of a compound of claim 1.

11. The method of claim 10 wherein the compound is administered in a dosage of from 0.002 to 100 mg per kg of body weight of the patient per day.

12. The method of claim 10 wherein the compound is 4-[4-(2-naphthalenyloxy)-1-piperidyl]-1-(4-fluorophenyl)-1-butanone or a pharmaceutically acceptable acid addition salt thereof.

13. The method of claim 10 wherein the compound is 4-[4-(1-naphthalenyloxy)-1-piperidyl]-1-(4-fluorophenyl)-1-butanone or a pharmaceutically acceptable acid addition salt thereof.

* * * * *